(12) United States Patent
Ng

(10) Patent No.: US 10,800,714 B2
(45) Date of Patent: Oct. 13, 2020

(54) LOW VOC AND LOW ODOR AROMATIC OIL

(71) Applicant: Dow Global Technologies LLC, Midland, MI (US)

(72) Inventor: Sze-Sze Ng, Midland, MI (US)

(73) Assignee: Dow Global Technologies LLC, Midland, MI (US)

(*) Notice: Subject to any disclaimer, the term of this patent is extended or adjusted under 35 U.S.C. 154(b) by 278 days.

(21) Appl. No.: 15/768,404

(22) PCT Filed: Oct. 17, 2016

(86) PCT No.: PCT/US2016/057352
§ 371 (c)(1),
(2) Date: Apr. 13, 2018

(87) PCT Pub. No.: WO2017/070048
PCT Pub. Date: Apr. 27, 2017

(65) Prior Publication Data
US 2018/0305268 A1      Oct. 25, 2018

Related U.S. Application Data

(60) Provisional application No. 62/243,426, filed on Oct. 19, 2015.

(51) Int. Cl.
| | |
|---|---|
| *C05G 3/90* | (2020.01) |
| *C05C 9/00* | (2006.01) |
| *C05F 3/00* | (2006.01) |
| *C05C 3/00* | (2006.01) |
| *C07F 9/22* | (2006.01) |
| *C07C 43/11* | (2006.01) |
| *C07C 43/115* | (2006.01) |

(52) U.S. Cl.
CPC .................. *C05G 3/90* (2020.02); *C05C 3/00* (2013.01); *C05C 3/005* (2013.01); *C05C 9/005* (2013.01); *C05F 3/00* (2013.01); *C07C 43/11* (2013.01); *C07C 43/115* (2013.01); *C07F 9/224* (2013.01); *Y02A 40/205* (2018.01); *Y02P 20/145* (2015.11)

(58) Field of Classification Search
CPC .. C05G 3/90; C05C 3/00; C05C 3/005; C05C 9/005; C07F 9/224; C07C 43/11; C07C 43/115; C05F 3/00; Y02P 20/145; Y02A 40/205
See application file for complete search history.

(56) References Cited

U.S. PATENT DOCUMENTS

| | | |
|---|---|---|
| 5,698,003 A | 12/1997 | Omilinsky et al. |
| 9,090,516 B2 | 7/2015 | Roberts |
| 9,096,476 B2 | 8/2015 | Roberts |
| 2014/0047883 A1* | 2/2014 | Gabrielson ............ C09K 15/06 71/28 |
| 2015/0143860 A1 | 5/2015 | McKnight et al. |
| 2016/0075613 A1 | 3/2016 | Gabrielson et al. |

FOREIGN PATENT DOCUMENTS

| | | |
|---|---|---|
| KR | 20100068649 A | 6/2010 |
| WO | 2008/000196 A1 | 1/2008 |
| WO | WO-2016170784 A1 * | 10/2016 ............ A01N 25/02 |

OTHER PUBLICATIONS

Dow Technical Data Sheet "DOWANOL Eph Glycol Ether" Published 2012.*
Dow Technical Data Sheet "DOWANOL EPH6" Published 2011.*

* cited by examiner

*Primary Examiner* — Jennifer A Smith
(74) *Attorney, Agent, or Firm* — Quarles & Brady LLP

(57) ABSTRACT

A low VOC, low vapor pressure, low flash point and nonfoaming fertilizer stabilizer composition comprises: (A) two or more glycol ethers of Formula 1 Each of $R^1$ and $R^3$ are independently hydrogen or phenyl with the proviso that $R^1$ and $R^3$ are not simultaneously hydrogen, n is an integer of 3-10, and $R^2$ is 90 to 100% hydrogen or 0 to 10% of one or more of methyl, ethyl or phenyl; and; and at least one fertilizer stabilizer, e.g., an N-alkyl thiophosphoric triamide.

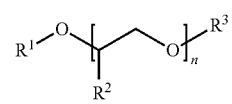

14 Claims, No Drawings

LOW VOC AND LOW ODOR AROMATIC OIL

BACKGROUND OF THE INVENTION

Nitrogen fertilizer is an important input in farming as it is correlated to yield. After nitrogen fertilizer is applied to the ground it can be lost through volatilization or leaching to ground water as the fertilizer undergoes the nitrogen cycle. To minimize loss of investment and environmental impact, nitrogen fertilizer is often treated with fertilizer stabilizer. Common fertilizer stabilizer products are for example AGROTAIN, N-SERVE, and NUTRISPHERE-N.

N-Alkyl thiophosphoric triamide urease inhibitor, e.g., N-butyl thiophosphoric triamide (NBPT), is used in agriculture to stabilize nitrogen fertilizer urea. It is most commonly formulated in a mixture of N-methyl-2-pyrrolidone (NMP) and propylene glycol (as in AGROTAIN™ by Koch). NMP is used as a crystal inhibitor but it has high toxicity. Other solvents are also known to be good solvents for NBPT, such as dimethyl sulfoxide (DMSO) (see US Published Patent Application 2015/0143860A1), benzyl alcohol (LIMUS™ by BASF), amino alcohol, and the like.

Some glycol ether solvents are known to be good solvents for NBPT (e.g., StabilureN™ by Agra, and see EP 2 032 589 B1). However, not all glycol ethers have the same properties. The alkyl glycol ether solvents are known to dissolve NBPT, but they have a strong odor, a low flash point, and a high volatile organic compound (VOC) content. Another type of alkyl glycol ether known as an effective NBPT carrier is a surfactant in nature, and it causes severe foaming issues in fertilizer solutions which require an antifoaming agent in the formulation (see U.S. Pat. Nos. 9,090,516 and 9,096,476). Based on these cited patents, glycol ether surfactant is functionally different from glycol ether solvents even though both are generically called glycol ethers. Glycol ether solvents provide varying degrees of chemical stability to NBPT depending on the specific structure. For example, a solution containing NBPT and dipropylene glycol methyl ether develops a strong yellow color within a month at ambient temperature.

An alternative solvent system for NBPT is desired, one that provides an improved user handling experience by reducing solvent odor and eliminating hazardous NMP, and reduces emission of air pollutants by lowering volatile organic content to a minimum level.

SUMMARY OF THE INVENTION

In one embodiment, the invention is a fertilizer stabilizer composition comprising:
(A) two or more glycol ethers of Formula 1

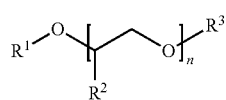

Formula 1 wherein
Each of $R^1$ and $R^3$ are independently hydrogen or phenyl with the proviso that $R^1$ and $R^3$ are not simultaneously hydrogen,
n is an integer of 3-10, and
$R^2$ is 90 to 100% hydrogen and 0 to 10% of one or more of methyl, ethyl or phenyl; and (B) at least one fertilizer stabilizer;
the fertilizer stabilizer composition characterized as having at least one of the following properties:
(1) a vapor pressure of less than or equal to (≤) 0.01 millimeters of mercury (mmHg) at 20° C. as measured by ASTM E1719,
(2) a flash point equal to or greater than (≥) 200° F. (93° C.) as measured by ASTM D3278,
(3) a viscosity less than or equal to (≤) 200 centipoise (cP) at 25° C. as measured by ASTM D445,
(4) a hydroxyl number from 100 to 1,000 as measured by ASTM D4274, and
(5) a VOC content less of than or equal to (≤) 50 weight percent (wt %) as measured by ASTM D6886.

In one embodiment the invention is a fertilizer composition comprising:
(A) the fertilizer stabilizer composition as described in the preceding paragraph, and
(B) a nitrogen-based fertilizer.

In one embodiment, the inventive fertilizer stabilizer composition comprises at least one of a N—$C_{1-6}$ alkyl thiophosphoric triamide, dicyandiamide, nitrapyrin, and salt of maleic-itaconic copolymer. In one embodiment, the inventive fertilizer stabilizer composition is free, or substantially free, of NMP.

The inventive fertilizer stabilizer compositions of this invention have a low flash point and odor profile, a low pour point for easy handling, a low VOC content, and they do not foam in fertilizer solutions, and they provide chemical and thermal stability to NBPT.

DETAILED DESCRIPTION OF THE PREFERRED EMBODIMENT

Definitions

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference), especially with respect to the disclosure of definitions (to the extent not inconsistent with any definitions specifically provided in this disclosure) and general knowledge in the art.

All percentages, preferred amounts or measurements, ranges and endpoints are inclusive, that is, "up to 10" includes 10. "At least" is equivalent to "greater than or equal to," and "at most" is, thus, equivalent "to less than or equal to." Numbers are approximate unless otherwise specifically noted. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus a range that has an advantageous lower limit combined with a most preferred upper limit is preferred for the practice of this disclosure. The term "advantageous" is used to denote a degree of preference more than required, but less than is denoted by the term "preferably." Numerical ranges are provided within this disclosure for, among other things, the amount of components in the various compositions of the invention.

Glycol Ethers

The fertilizer stabilizer compositions of this invention comprise two or more glycol ethers of Formula 1

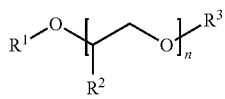

Formula 1 wherein

Each of $R^1$ and $R^3$ are independently hydrogen or phenyl with the proviso that $R^1$ and $R^3$ are not simultaneously hydrogen, n is an integer of 3-10, and $R^2$ is 90 to 100% hydrogen and 0 to 10% of one or more of methyl, ethyl or phenyl. In one embodiment, if $R^1$ is hydrogen, then $R^3$ is phenyl. In one embodiment, if $R^1$ is phenyl, then $R^3$ is hydrogen. In one embodiment, both $R^1$ and $R^3$ are phenyl. In one embodiment, n is an integer of 3, or 4, or 5, or 6, or 7, or 8, or 9. In one embodiment, n is an integer of 3 to 4, or 5, or 6, or 7, or 8, or 9, or 10; or of 4 to 5, or 6, or 7, or 8, or 9 or 10; or of 5 to 6, or 7, or 8, or 9, or 10; of 6 to 7, or 8, or 9, or 10; or of 7 to 8, or 9, or 10; or of 8 to 9 or 10; or of 9 or 10. In one embodiment, $R^2$ is at least 91%, or 92%, or 93%, or 94%, or 95%, or 96%, or 97%, or 98%, or 99% to 100% hydrogen. In one embodiment, $R^2$ is at least 1%, or 2%, or 3%, or 4%, or 5%, or 6%, or 7%, or 8%, or 9% to 10% one or more of methyl, ethyl or phenyl. "At least 91%, or 92%, or . . . " means that the value of $R^2$ can be a whole number, e.g., 91, 92, etc., or a fractional number, e.g., 91.1, or 92.1, etc. "At least 1%, or 2%, or . . . " means that the value of $R^2$ can be a whole number, e.g., 1, 2, etc., or a fractional number, e.g., 1.1, or 2.1, etc.

"Two or more glycol ethers of Formula 1" means that the liquid composition comprises at least two distinct glycol ethers of Formula 1, e.g., a first glycol ether in which $R^1$ is hydrogen and a second glycol ether in which $R^1$ is phenyl and all other substituents or components of the two glycol ethers are the same; or a first glycol ether in which n is 3 and a second glycol ether in which n is 10 and all other substituents or components of the two glycol ethers are the same; etc. The glycol ethers can differ from one another in more than one substituent or component, and the fertilizer stabilizer composition can comprise any number of different glycol ethers of Formula 1.

Based on the total amount of glycol ethers in the fertilizer stabilizer composition, the amount of any on glycol ether can vary widely. Typically, no one glycol ether comprises more than 99 wt % of the total amount of glycol ethers in the fertilizer stabilizer composition, more typically no more than 90, or 80, or 70, or 60, or 50 wt % of the total amount of glycol ethers in the fertilizer stabilizer composition. In one embodiment, glycols other than those of Formula 1, e.g., ethylene and/or propylene glycol, glycerol, polyalkylene glycol, etc., may also be present, and these can be present in either a majority or minority amount of the total glycol content of the fertilizer stabilizer composition, but typically these are present in a minority amount, i.e., they constitute less than 50 wt %, more typically less than 25 wt %, of the total glycol content of the fertilizer stabilizer composition.

The glycol ethers of Formula 1 are known compounds and are commercially available, such as DOWANOL™ EPh6.

Fertilizer Stabilizers

The fertilizer stabilizer compositions of this invention comprise one or more fertilizer stabilizers. These stabilizers include, but are not limited to, $N-C_{1-6}$ alkyl thiophosphoric triamide, dicyandiamide, nitrapyrin, and salt of maleic-itaconic copolymer. Regarding $N-C_{1-6}$ alkyl thiophosphoric triamide, the alkyl can be linear or branched, and preferably the alkyl is propyl or butyl. In one embodiment, the fertilizer stabilizer compositions comprise just one fertilizer stabilizer, and in one embodiment that fertilizer stabilizer is a $N-C_{1-6}$ alkyl thiophosphoric triamide, preferably N-(n-butyl) thiophosphoric triamide (NBPT) or N-(n-propyl) thiophosphoric triamide (NPPT).

Fertilizer Stabilizer Compositions

In one embodiment, the fertilizer stabilizer compositions of this invention comprise 0.01 to 60 wt %, preferably 0.01 to 35 wt % and more preferably 0.01 to 25 wt %, fertilizer stabilizer and 40-99.99 wt %, preferably 65 to 99.99 wt % and more preferably 75 to 99.99 wt % glycol ether.

The fertilizer stabilizer compositions of this invention are liquid at ambient conditions (20-25° C. and atmospheric pressure), and are typically a solution, i.e., without any significant particulate content. In other words, the fertilizer stabilizer is typically soluble in the glycol mixture, i.e., the two or more glycol ethers of Formula 1 and any additional glycols/solvents that may be present.

In one embodiment, the fertilizer stabilizer compositions of this invention have a low volatile organic compound (VOC) content, typically less of than or equal to (≤) 50 weight percent (wt %), more typically ≤30 wt %, or ≤10 wt %, or ≤4 wt %, as measured by ASTM D6886.

In one embodiment, the fertilizer stabilizer compositions of this invention have a low vapor pressure, typically less than or equal to (≤) 0.01 millimeters of mercury (mmHg), or ≤0.001 mmHg, or ≤0.0001 mmHg, at 20° C. as measured by ASTM E1719.

In one embodiment, the fertilizer stabilizer compositions of this invention have a viscosity less than or equal to (≤) 200, or ≤100, centipoise (cP) at 25° C. as measured by ASTM D445.

In one embodiment, the fertilizer stabilizer compositions of this invention have a flash point equal to or greater than (≥) 200° F. (93° C.), or ≥250° F. (121° C.), as measured by ASTM D3278.

In one embodiment, the fertilizer stabilizer compositions of this invention have a hydroxyl number from 100 to 1,000, or from 100 to 800, or from 100 to 600, as measured by ASTM D4274.

In one embodiment, the fertilizer stabilizer compositions of this invention have at least two, or at least three, or at least four, or all five of the properties of VOC content, vapor pressure, viscosity, flash point and hydroxyl number as described in the previous embodiments.

In one embodiment, the fertilizer stabilizer compositions of this invention consist essentially of 0.01 to 60 wt %, preferably 0.01 to 35 wt % and more preferably 0.01 to 25 wt %, of fertilizer stabilizer and 40-99.99 wt %, preferably 65 to 99.99 wt % and more preferably 75 to 99.99 wt %, two or more glycol ether of Formula 1.

In one embodiment, the fertilizer stabilizer compositions of this invention consist essentially of 0.01 to 60 wt %, preferably 0.01 to 35 wt % and more preferably 0.01 to 25 wt %, of at least one of $N-C_{1-6}$ alkyl thiophosphoric triamide, dicyandiamide nitrapyrin and salt of maleic-itaconic copolymer, and 40-99.99 wt %, preferably 65 to 99.99 wt % and more preferably 75 to 99.99 wt %, of two or more glycol ethers of Formula 1.

In one embodiment, the fertilizer stabilizer compositions of this invention consist essentially of 0.01 to 60 wt %, preferably 0.01 to 35 wt % and more preferably 0.01 to 25 wt %, of at least one of N-(n-butyl) thiophosphoric triamide (NBPT) or N-(n-propyl) thiophosphoric triamide (NPPT), and 40-99.99 wt %, preferably 65 to 99.99 wt % and more preferably 75 to 99.99 wt % of two or more glycol ethers of Formula 1.

In one embodiment, the fertilizer stabilizer compositions of this invention consist of 0.01 to 60 wt %, preferably 0.01 to 35 wt % and more preferably 0.01 to 25 wt %, of fertilizer stabilizer and 40-99.99 wt %, preferably 65 to 99.99 wt % and more preferably 75 to 99.99 wt %, of two or more of glycol ethers of Formula 1.

In one embodiment, the fertilizer stabilizer compositions of this invention consist of 0.01 to 60 wt %, preferably 0.01 to 35 wt % and more preferably 0.01 to 25 wt %, of at least one of N—$C_{1-6}$ alkyl thiophosphoric triamide, dicyandiamide nitrapyrin and salt of maleic-itaconic copolymer, and 40-99.99 wt %, preferably 65 to 99.99 wt % and more preferably 75 to 99.99 wt %, of two or more glycol ethers of Formula 1.

In one embodiment, the fertilizer stabilizer compositions of this invention consist of 0.01 to 40 wt %, preferably 0.01 to 25 wt %, at least one of N-(n-butyl) thiophosphoric triamide (NBPT) or N-(n-propyl) thiophosphoric triamide (NPPT), and 40-99.99 wt %, preferably 65 to 99.99 wt % and more preferably 75 to 99.99 wt %, of two or more glycol ethers of Formula 1.

In one embodiment, the fertilizer stabilizer composition is free, or substantially free, of N-methyl-2-pyrrolidone (NMP). "Free, or substantially free, of" means that the fertilizer stabilizer composition contains less than 1, or less than 0.5, or less than 0.1, or less than 0.05, or less than 0.01, wt % of NMP, based on the weight of the fertilizer stabilizer composition.

Fertilizer Composition

In one embodiment the invention is a fertilizer composition comprising:
(A) the fertilizer stabilizer composition as described above, and
(B) a nitrogen-based fertilizer.

Any nitrogen-based fertilizer can be used in the practice of this embodiment of the invention, and representative nitrogen-based fertilizers include, but are not limited to, urea, urea ammonium nitrate, ammonia, manure and the like. The fertilizer stabilizer composition can be applied to the nitrogen-based fertilizer in any convenient manner, e.g., spraying the fertilizer stabilizer composition onto solid fertilizer granules and then applying the granules onto or into a soil surface, or mix the fertilizer stabilizer composition directly with one or more liquid fertilizers before spraying the mixture onto a field, or injecting into the fertilizer stabilizer composition into the soil with ammonia, etc. The amount of fertilizer stabilizer composition that is applied to the nitrogen-based fertilizer can vary to convenience, but typically between 0.01 and 10, more typically between 0.01 and 1, and even more typically between 0.01 and 0.5, wt % of the fertilizer stabilizer composition is applied to the nitrogen-based fertilizer, based on the weight of the nitrogen-based fertilizer.

EXAMPLES

Example 1

NBPT Solubility and Storage Study

Recipe: 20 wt % NBPT/80 wt % Solvent

NBPT and solvent are added to a glass vial. The mixture is shaken on an orbital shaker at room temperature (20-25° C.). The sample is inspected to determine if all NBPT dissolved at room temperature.

Each NBPT mixture is stored at three temperatures, room temperature (20-25° C.), 55° C., and −20° C. for 4 weeks to evaluate storage stability at elevated, ambient, and sub-ambient conditions. After 4 weeks of storage, the samples are visually inspected for (1) color, which is an indication of degradation, and (2) crystal formation, which is an indicator of insufficient solvency to carry 20 wt % NBPT.

NBPT is considered compatible with a solvent if the mixture remained clear, crystal free, and flowable at −20° C. for four weeks, and has little color (colorless or pale yellow) after four weeks at 55° C.

Only two glycol ethers are identified as compatible with NBPT: methyl CARBITOL™ (as described in WO 2014/028767 A1 and WO 2008/000196 A1, an alkyl glycol ether not of Formula 1, and a comparative sample) and DOWANOL™ EPh6 (a mixture of glycol ethers comprising at least two structures of Formula 1, and an inventive sample). The flash point and vapor pressure of the solvents which produced compatible NBPT mixtures are listed in Table 1 which reports that methyl CARBITOL™ has a low flash point of 197° F. (91.7° C.) and high vapor pressure of >0.1 mmHg at 20° C., and that DOWANOL™ EPh6 has a high flash point of >300° F. (149° C.) and a low vapor pressure of <0.0001 mmHg at 20° C.

Also note that DOWANOL™ PPH, DOWANOL™ EPH, DOWANOL™ DiPPH, DOWANOL™ DiEPH, and DOWANOL™ DPH 225—all aromatic glycol ethers which according to Formula 1 have n=1 (PPh and Eph), n=2 (DiEPh and DiPPh), or n=1 and 2 (DPH 255), are not able to produce a NBPT mixture that provides sufficient solvency to carry 20 wt % NBPT, as the NBPT mixture with these solvents does not produce a solution that is free of crystal or is flowable at −20° C. This indicates that DOWANOL™ EPh6 is a unique aromatic glycol ether mixture for use as a NBPT solvent.

TABLE 1

NBPT Solubility Test Results

| # | Type | Solvent | RT | −20° C. 4 wks | 55° C. 4 wks Color | Solvent flash point (° F./° C.) | Vapor pressure mmHg at 20° C. |
|---|---|---|---|---|---|---|---|
| 1 | P-Series | DOWANOL PM | ○ | X | | | |
| 2 | glycol ethers | DOWANOL DPM | ○ | X | | | |
| 3 | | DOWANOL TPM | ○ | X | | | |
| 4 | | DOWANOL PMA | hazy | X | | | |
| 5 | | DOWANOL DPMA | hazy | X | | | |
| 6 | | DOWANOL PnP | ○ | X | | | |
| 7 | | DOWANOL DPnP | ○ | X | | | |

TABLE 1-continued

NBPT Solubility Test Results

| # | Type | Solvent | RT | −20° C. 4 wks | 55° C. 4 wks | Color | Solvent flash point (° F./° C.) | Vapor pressure mmHg at 20° C. |
|---|---|---|---|---|---|---|---|---|
| 8 | | DOWANOL PnB | hazy | X | | | | |
| 9 | | DOWANOL DPnB | X | X | | | | |
| 10 | | DOWANOL TPnB | X | X | | | | |
| 11 | | DOWANOL PPh | ○ | X | | | | |
| 12 | | DOWANOL DiPPh | X | X | | | | |
| 13 | | DOWANOL PGDA | X | X | | | | |
| 14 | | PROGLYDE DMM | ○ | X | | | | |
| 15 | E-Series | Methyl CARBITOL | ○ | ○ | pale yellow | 197/92 | 0.23 | |
| 16 | glycol ethers | Methoxytriglycol | ○ | ○ | orange | | | |
| 17 | | CARBITOL | ○ | ○ | red | | | |
| 18 | | Ethoxytriglycol | ○ | ○ | red | | | |
| 19 | | Propyl CELLOSOLVE | ○ | X | | | | |
| 20 | | Butyl CELLOSOLVE | ○ | X | | | | |
| 21 | | Butyl CARBITOL | ○ | X | | | | |
| 22 | | Butoxytriglycol | ○ | ○ | red | | | |
| 23 | | Butyl CELLOSOLVE Acetate | X | X | | | | |
| 24 | | Butyl CARBITOL Acetate | ○ | X | | | | |
| 25 | | Hexyl CELLOSOLVE | ○ | X | | | | |
| 26 | | Hexyl CARBITOL | ○ | X | | | | |
| 27 | | DOWANOL EPh | ○ | X | | | | |
| 28 | | DOWANOL DiEPh | ○ | X | | | | |
| 29 | | DOWANOL EPh6 | ○ | ○ | pale yellow | >300/>149 | <0.0001 | |
| 30 | | DOWANOL DPH 255 | ○ | X | | | | |

○ = flowable and crystal free
X = either frozen or contains crystals

Example 2

Foam Level of Nitrogen Fertilizer Solutions Containing NBPT Mixtures

Recipe: 20 wt % NBPT/80 wt % Carrier

WO 2014/028715 A1, and U.S. Pat. No. 9,090,516, teach solvent-free NBPT composition that use a surfactant as the carrier. The problem with using surfactant as a NBPT carrier is foam generation. As is well-known in the fertilizer industry, an observable amount of foam can be generated in an aqueous solution of a surfactant. Solvent does not generate foam because it is not a surfactant. This example demonstrates that DOWANOL™ EPh6 does not generate foam.

NBPT mixtures (#31-36) are prepared by mixing NBPT and carrier in a glass vial on an orbital shaker at room temperature (20-25° C.). As reported in Table 2, mixtures #31-35 are clear and colorless while #36 is orange in color, an indication of degradation.

TABLE 2

NBPT and Carrier Mixtures

| Component | 31 | 32 | 33 | 34 | 35 | 36 |
|---|---|---|---|---|---|---|
| NBPT (g) | 20% | 20% | 20% | 20% | 20% | 20% |
| DOWANOL EPh6 (g) | 80% | | | | | |
| BIOSOFT N25-3 (g) | | 80% | | | | |
| TERGITOL 15-S-5 (g) | | | 80% | | | |
| TERGITOL 15-S-9 (g) | | | | 80% | | |
| TERGITOL NP-9 (g) | | | | | 80% | |
| TAE 20EO (g) | | | | | | 80% |
| Color | clear, colorless | clear, colorless | clear, colorless | clear, colorless | clear, colorless | clear, orange |

Sixty microliters of NBPT mixtures (#31-36) is added to 30 milliliters (mL) of 342 parts per million (ppm) World Health Organization (WHO) standard hard water. The mixtures are shaken together on the same sample rack for 15 seconds to generate foam. The amount of foam generated immediately (time=0) is measured with a ruler. The height of the foam is recorded at time=0, time=15 minutes, and time=60 minutes. The higher the foam height, the more foam generated.

Similarly, sixty microliters of NBPT mixtures (#31-36) is added to 30 mL of 28-0-0 nitrogen-phosphorus-potassium fertilizer. The mixtures are shaken together on the same sample rack for 15 seconds to generate foam. The amount of foam generated immediately (time=0) is measured with a ruler. The height of the foam is recorded at time=0, time=15 minutes, and time=60 minutes. The higher the foam height, the more foam generated.

As summarized in Table 3 below, NBPT mixture #31 (prepared using DOWANOL™ EPh6 as solvent) does not generate any significant amount of foam (<2 mm foam) in hard water and in 28-0-0 nitrogen fertilizer. On the other hand, all other examples (#32-#36) with surfactants as NBPT carrier generate a large amount of foam in hard water and in nitrogen fertilizer. Hence, DOWANOL™ EPh6 is not a surfactant as it is not the type of carrier described in WO 2014/028715 A1, and U.S. Pat. No. 9,090,516.

TABLE 3

Foaming Test Results of NBPT and a Nitrogen-Based Fertilizer

| Time after shaking (min) | NBPT Mixture | Foam height (mm) of NBPT mixture in 342 ppm hard water | Foam height (mm) of NBPT mixture in 28-0-0 fertilizer |
|---|---|---|---|
| 0 | 31 | 1 | 0 |
| | 32 | 10 | 5 |
| | 33 | 12 | 5 |
| | 34 | 50 | 37 |
| | 35 | 50 | 35 |
| | 36 | 40 | 25 |
| 15 | 31 | 0 | 0 |
| | 32 | 7 | 4 |

TABLE 3-continued

Foaming Test Results of NBPT and a Nitrogen-Based Fertilizer

| Time after shaking (min) | NBPT Mixture | Foam height (mm) of NBPT mixture in 342 ppm hard water | Foam height (mm) of NBPT mixture in 28-0-0 fertilizer |
|---|---|---|---|
| | 33 | 8 | 3 |
| | 34 | 50 | 24 |
| | 35 | 50 | 25 |
| | 36 | 20 | 20 |
| 60 | 31 | 0 | 0 |
| | 32 | 6 | 4 |
| | 33 | 5 | 2 |
| | 34 | 30 | 9 |
| | 35 | 30 | 25 |
| | 36 | 9 | 11 |

What is claimed is:

1. A fertilizer stabilizer composition comprising:
(A) two or more glycol ethers of Formula 1

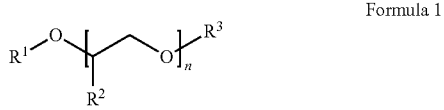

Formula 1 wherein
Each of $R^1$ and $R^3$ are independently hydrogen or phenyl with the proviso that $R^1$ and $R^3$ are not simultaneously hydrogen,
n is an integer of 3-10, and
$R^2$ is 90 to 100% hydrogen or 0 to 10% of one or more of methyl, ethyl or phenyl;
and
(B) at least one fertilizer stabilizer;
the fertilizer stabilizer composition characterized as having at least one of the following properties:
(1) a vapor pressure of less than or equal to ($\leq$)0.01 millimeters of mercury (mmHg) at 20° C. as measured by ASTM E1719,
(2) a flash point equal to or greater than ($\geq$)200° F. (93° C.) as measured by ASTM D3278,
(3) a viscosity less than or equal to ($\leq$)200 centipoise (cP) at 25 ° C. as measured by ASTM D445,
(4) a hydroxyl number from 100 to 1,000 as measured by ASTM D4274, and
(5) a VOC content less of than or equal to ($\leq$)50 weight percent (wt %) as measured by ASTM D6886.

2. The fertilizer stabilizer composition of claim 1 in which the at least one fertilizer stabilizer is at least one of:
(1) a N—$C_{1-6}$ alkyl thiophosphoric triamide,
(2) dicyandiamide,
(3) nitrapyrin, and
(4) salt of maleic-itaconic copolymer.

3. The fertilizer stabilizer composition of claim 1 comprising 40-99.99 wt % of the two or more glycol ethers of Formula 1, and 0.01-60 wt % of the fertilizer stabilizer.

4. The fertilizer stabilizer composition of claim 1 in which $R^1$ of Formula 1 is hydrogen and $R^3$ of Formula 1 is phenyl.

5. The fertilizer stabilizer composition of claim 1 in which $R^1$ of Formula 1 is phenyl and $R^3$ of Formula 1 is hydrogen.

6. The fertilizer stabilizer composition of claim 1 in which the fertilizer stabilizer is N—$C_{1-6}$ alkyl thiophosphoric triamide, and the alkyl is propyl or butyl.

7. The fertilizer stabilizer composition of claim 1 further comprising glycols other than the glycol ethers of Formula 1.

8. The fertilizer stabilizer composition of claim 1 having at least two of the properties of vapor pressure, flash point, viscosity, hydroxyl number and VOC content.

9. The fertilizer stabilizer composition of claim 1 having at least three of the properties of vapor pressure, flash point, viscosity, hydroxyl number and VOC content.

10. The fertilizer stabilizer composition of claim 1 having at least four of the properties of vapor pressure, flash point, viscosity, hydroxyl number and VOC content.

11. The fertilizer stabilizer composition of claim 1 having all five of the properties of vapor pressure, flash point, viscosity, hydroxyl number and VOC content.

12. A fertilizer composition comprising:
(A) the fertilizer stabilizer composition of claim 2, and
(B) a nitrogen-based fertilizer.

13. The fertilizer composition of claim 12 in which the nitrogen-based fertilizer is at least one of urea, urea ammonium nitrate, ammonia and manure.

14. The fertilizer composition of claim 12 in which the fertilizer stabilizer composition comprises between 0.01 and 10 wt % of the fertilizer composition based on the weight of the nitrogen-based fertilizer.

* * * * *